US010115315B2

(12) United States Patent
Jonak et al.

(10) Patent No.: US 10,115,315 B2
(45) Date of Patent: Oct. 30, 2018

(54) SYSTEMS AND METHODS FOR REQUESTING FLIGHT PLAN CHANGES ONBOARD AN AIRCRAFT DURING FLIGHT

(71) Applicant: HONEYWELL INTERNATIONAL INC., Morris Plains, NJ (US)

(72) Inventors: Jaroslav Jonak, Brno (CZ); Vitezslav Cip, Zubri (CZ); Karel Mundel, Vrane nad Vltavou (CZ); Petr Vesely, Horni Marsov (CZ)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/457,566

(22) Filed: Mar. 13, 2017

(65) Prior Publication Data

US 2018/0261104 A1  Sep. 13, 2018

(51) Int. Cl.
| | | |
|---|---|---|
| *G01S 13/91* | (2006.01) | |
| *G08G 5/00* | (2006.01) | |
| *B64D 43/00* | (2006.01) | |

(52) U.S. Cl.
CPC ........... *G08G 5/0039* (2013.01); *B64D 43/00* (2013.01); *G08G 5/0021* (2013.01); *G08G 5/0047* (2013.01); *G08G 5/0091* (2013.01)

(58) Field of Classification Search
USPC ....................................................... 701/120
See application file for complete search history.

(56) References Cited

U.S. PATENT DOCUMENTS

| | | | |
|---|---|---|---|
| 5,574,467 A | 11/1996 | Saunders | |
| 5,574,647 A | 11/1996 | Liden | |
| 6,744,382 B1 * | 6/2004 | Lapis | G01C 23/005 340/963 |
| 8,014,907 B2 | 9/2011 | Coulmeau | |
| 8,423,272 B2 | 4/2013 | Judd et al. | |

(Continued)

FOREIGN PATENT DOCUMENTS

| | | |
|---|---|---|
| EP | 1947624 A1 | 7/2008 |
| EP | 2388759 A2 | 11/2011 |

(Continued)

OTHER PUBLICATIONS

Amendment 45 to the International Standards Rules of the AIR (Annex 2 to the Convention on International Civil Aviation) Tenth Edition—Jul. 2005.

(Continued)

*Primary Examiner* — Tyler D Paige
(74) *Attorney, Agent, or Firm* — Lorenz & Kopf, LLP

(57) ABSTRACT

A method for generating a request onboard an aircraft, by a processor communicatively coupled to system memory and a communication device, is provided. In response to a requested change to a current flight plan, the method automatically generates, by the processor, a text-based clearance request for the requested change, the text-based clearance request comprising aircraft identification and the requested change, and the requested change comprising at least one of a new cruising level, a new cruising speed at the new cruising level, flight rules, a new route description, and revised time estimates associated with waypoints of the current flight plan; and transmits the text-based clearance request, via the communication device.

20 Claims, 5 Drawing Sheets

(56) References Cited

U.S. PATENT DOCUMENTS

| | | | |
|---|---|---|---|
| 8,600,588 B2 | 12/2013 | Del Amo Blanco et al. | |
| 8,892,275 B2 | 11/2014 | Constans et al. | |
| 9,290,262 B2 | 3/2016 | Laso-Leon | |
| 9,330,573 B2 | 5/2016 | Brandao et al. | |
| 2004/0078136 A1 | 4/2004 | Cornell et al. | |
| 2005/0049762 A1* | 3/2005 | Dwyer | G01C 23/00 701/3 |
| 2008/0163093 A1* | 7/2008 | Lorido | G01C 23/00 715/771 |
| 2008/0167885 A1* | 7/2008 | Judd | G08G 5/0013 701/120 |
| 2008/0195309 A1* | 8/2008 | Prinzel, III | G01C 23/00 701/532 |
| 2009/0089693 A1* | 4/2009 | Fahy | G06F 17/243 715/764 |
| 2011/0166772 A1* | 7/2011 | Ferro | G08G 5/0013 701/120 |
| 2011/0246053 A1* | 10/2011 | Coulmeau | G08G 5/0013 701/120 |
| 2012/0078447 A1* | 3/2012 | McGuffin | G08G 5/0021 701/3 |
| 2012/0079398 A1* | 3/2012 | McGuffin | G06F 3/048 715/752 |
| 2012/0095623 A1* | 4/2012 | Barral | G01C 23/005 701/4 |
| 2012/0215435 A1* | 8/2012 | Subbu | G08G 5/0013 701/120 |
| 2012/0265374 A1 | 10/2012 | Yochum | |
| 2013/0184978 A1* | 7/2013 | Subbu | G08G 5/0013 701/120 |
| 2014/0039734 A1 | 2/2014 | Ramaiah et al. | |
| 2014/0244077 A1 | 8/2014 | Laso-Leon et al. | |
| 2015/0081292 A1* | 3/2015 | Populus | G08G 5/0013 704/235 |
| 2015/0199906 A1* | 7/2015 | Judy | G08G 5/003 701/3 |
| 2015/0213720 A1* | 7/2015 | Axtell | G08G 5/0095 701/120 |
| 2015/0323933 A1 | 11/2015 | Darbois | |
| 2016/0019796 A1 | 1/2016 | Agrawal | |
| 2016/0125744 A1 | 5/2016 | Shamasundar et al. | |

FOREIGN PATENT DOCUMENTS

| | | |
|---|---|---|
| EP | 2631732 A1 | 8/2013 |
| EP | 2690613 A2 | 1/2014 |

OTHER PUBLICATIONS

USPTO Office Action for U.S. Appl. No. 15/017,782 dated May 4, 2017.

Extended EP Search Report for Application No. 17151890.5-1557 dated May 7, 2017.

USPTO Notice of Allowance for U.S. Appl. No. 15/017,782 dated Sep. 6, 2017.

Murrieta-Mendoza, A.; Flight Altitude Optimization Using Genetic Algorithms Considering Climb and Descent Costs in Cruise with Flight Plan Information; The Research Laboratory in Active Controls, Avionics and Aeroservoelasticity (LARCASE) 2015.

Ng, H.K et al.; A Practical Approach for Optimizing Aircraft Trajectories in Winds; University of California, NASA Ames Research Center Jun. 21, 2011.

Extended EP Search Report for Application No. 18160831.6-1203 dated Jul. 17, 2018.

* cited by examiner

SYSTEMS AND METHODS FOR REQUESTING FLIGHT PLAN CHANGES ONBOARD AN AIRCRAFT DURING FLIGHT

TECHNICAL FIELD

Embodiments of the subject matter described herein relate generally to requesting flight plan changes onboard an aircraft during flight. More particularly, embodiments of the subject matter relate to generating and transmitting a text-based request message for flight plan changes.

BACKGROUND

During flight, changes to a flight plan are generally communicated verbally, via radio telephony onboard the aircraft. Such flight plan changes are communicated to Air Traffic Control (ATC), which clears the requested flight plan changes for use by communicating with other aircraft in the area. Such back-and-forth voice transmissions require a significant amount of time, resulting in delays to necessary flight plan changes. Additionally, both vertical and lateral flight plan changes involve a significant amount of information for communication, resulting in increased potential for misinterpretation and miscommunication from ATC during secondary transmissions.

Accordingly, it is desirable to reduce the time required to clear flight plan changes, and to reduce the probability of misinterpretation and miscommunication of requested flight plan changes. Furthermore, other desirable features and characteristics will become apparent from the subsequent detailed description and the appended claims, taken in conjunction with the accompanying drawings and the foregoing technical field and background.

BRIEF SUMMARY

Some embodiments of the present disclosure provide a method for generating a request onboard an aircraft, by a processor communicatively coupled to system memory and a communication device. In response to a requested change to a current flight plan, the method automatically generates, by the processor, a text-based clearance request for the requested change, the text-based clearance request comprising aircraft identification and the requested change, and the requested change comprising at least one of a new cruising level, a new cruising speed at the new cruising level, flight rules, a new route description, and revised time estimates associated with waypoints of the current flight plan; and transmits the text-based clearance request, via the communication device.

Some embodiments of the present disclosure provide a system for generating a request onboard an aircraft. The system includes system memory; a communication device, configured to transmit data from the aircraft to air traffic control (ATC); and at least one processor, communicatively coupled to the system memory and the communication device. In response to a requested change to a current flight plan, the at least one processor is configured to automatically generate a text-based clearance request for the requested change, the text-based clearance request comprising aircraft identification and the requested change, and the requested change comprising at least one of a new cruising level, a new cruising speed at the new cruising level, flight rules, a new route description, and revised time estimates associated with waypoints of the current flight plan; and transmit the text-based clearance request, via the communication device.

Some embodiments of the present disclosure provide a non-transitory, computer-readable medium containing instructions thereon, which, when executed by a processor, perform a method. The method receives a request for one or more changes to a current flight plan, by the processor onboard an aircraft; generates, by the processor, a text message comprising a clearance request for the one or more changes to the current flight plan; and transmits the text message, via a communication device communicatively coupled to the processor.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter presented herein relates to systems and methods for creating and transmitting a text-based clearance request message for changes to a current flight plan, onboard an aircraft and during flight. More specifically, when changes to a current flight plan are necessary, the present disclosure provides a system for automatically generating a text message, using a predetermined and standardized format, and transmitting the standardized text message to air traffic control (ATC) for clearance approval. The clearance request text message may also potentially be transmitted to other aircraft affected by the change in flight plan for the first aircraft.

Certain terminologies are used with regard to the various embodiments of the present disclosure. A clearance request is a message transmitted to air traffic control (ATC) from an aircraft requesting approval for one or more particular aircraft operations. A change to a flight plan is any diversion from a current vertical profile and/or lateral profile of the aircraft requesting the change. A text-based clearance request message is a text message that is automatically generated by a computing device onboard an aircraft in response to a requested change to a current flight plan. The text-based clearance message may include a plurality of predefined data fields and may use particular terminology or acronyms to conform to a standardized format used for ease of interpretation and understanding of the contents of the text-based clearance request message.

Figure 1:
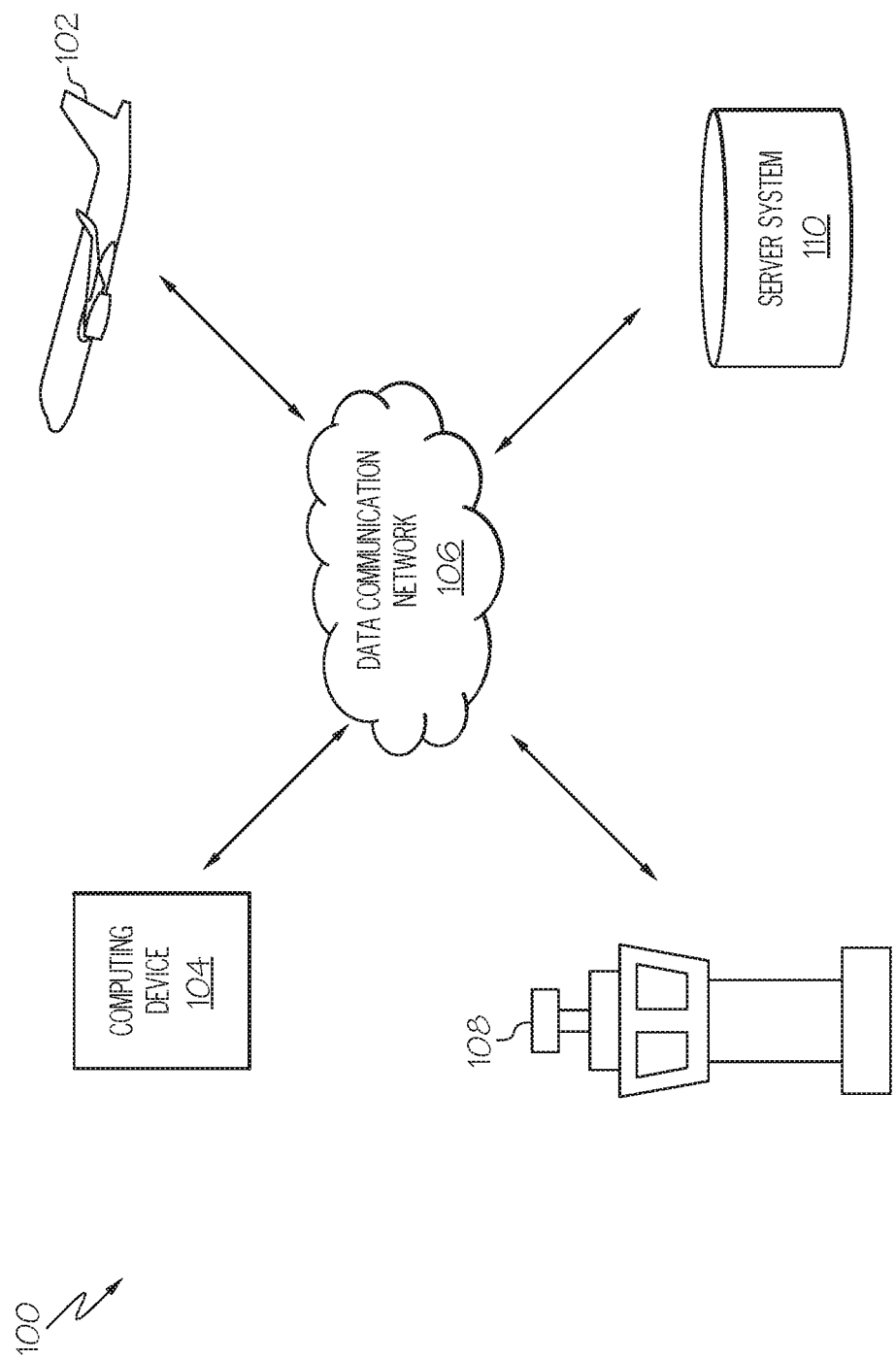
FIG. 1 is a diagram of a system for automatically generating clearance requests, in accordance with the disclosed embodiments.

Turning now to the figures, FIG. 1 is a diagram of a system 100 for automatically generating clearance requests, in accordance with the disclosed embodiments. The system 100 operates to obtain information associated with requested changes to a current flight plan for an aircraft 102 and, in response to the changes, to generate and transmit a text-based clearance request message such that a new flight plan based on the changes may be approved and communicated to other aircraft in the area. The system 100 may include, without limitation, a computing device 104 that communicates with one or more avionics systems onboard the aircraft 102 and at least one server system 110, via a data communication network 106. In practice, certain embodiments of the system 100 may include additional or alternative elements and components, as desired for the particular application.

The aircraft 102 may be any aviation vehicle for which a flight plan or flight profile (e.g., vertical flight profile or lateral flight profile) is used during flight, and which includes one or more avionics systems which may include a Flight Management System (FMS), navigation devices, weather radar, and the like. The aircraft 102 may be implemented as an airplane, helicopter, spacecraft, hovercraft, or the like.

The computing device 104 may be implemented by any computing device that includes at least one processor, some form of memory hardware, a user interface, and communication hardware. For example, the computing device 104 may be implemented using a personal computing device, such as a tablet computer, a laptop computer, a personal digital assistant (PDA), a smartphone, or the like. In this scenario, the computing device 104 is capable of storing, maintaining, and executing an Electronic Flight Bag (EFB) application configured to generate and transmit text messages associated with changes to a current flight plan, such as a text-based clearance request message. In other embodiments, the computing device 104 may be implemented using a computer system onboard the aircraft 102, which is configured to generate and transmit text-based clearance request messages.

The server system 110 may include any number of application servers, and each server may be implemented using any suitable computer. In some embodiments, the server system 110 includes one or more dedicated computers. In some embodiments, the server system 110 includes one or more computers carrying out other functionality in addition to server operations. The server system 110 may store and provide any type of data used to identify necessary changes to a current flight plan, determine an optimal or secondary flight plan, generate a text-based clearance request message, or the like. Such data may include, without limitation: flight plan data, meteorological data, aircraft identification data, and other data compatible with the computing device 104.

The computing device 104 is usually located onboard the aircraft 102, and the computing device 104 communicates with the one or more avionics systems onboard the aircraft 102 via wired and/or wireless communication connection. The computing device 104 and the server system 110 are generally disparately located, and the computing device 104 communicates with the server system 110 via the data communication network 106 and/or via communication mechanisms onboard the aircraft 102.

The data communication network 106 may be any digital or other communications network capable of transmitting messages or data between devices, systems, or components. In certain embodiments, the data communication network 106 includes a packet switched network that facilitates packet-based data communication, addressing, and data routing. The packet switched network could be, for example, a wide area network, the Internet, or the like. In various embodiments, the data communication network 106 includes any number of public or private data connections, links or network connections supporting any number of communications protocols. The data communication network 106 may include the Internet, for example, or any other network based upon TCP/IP or other conventional protocols. In various embodiments, the data communication network 106 could also incorporate a wireless and/or wired telephone network, such as a cellular communications network for communicating with mobile phones, personal digital assistants, and/or the like. The data communication network 106 may also incorporate any sort of wireless or wired local and/or personal area networks, such as one or more IEEE 802.3, IEEE 802.16, and/or IEEE 802.11 networks, and/or networks that implement a short range (e.g., Bluetooth) protocol. For the sake of brevity, conventional techniques related to data transmission, signaling, network control, and other functional aspects of the systems (and the individual operating components of the systems) may not be described in detail herein.

During typical operation, the computing device 104 may operate to automatically obtain changes to a current flight plan or to receive, via a user interface of the computing device 104, user-requested changes to a flight plan. In response to the received changes, the computing device 104 then generates a text message, according to a standard format, which includes details relevant to a clearance request for the aircraft 102 to pursue an alternate flight plan that includes the received changes. The computing device 104 further operates to transmit the generated text message to air traffic control (ATC) 108, and potentially to transmit the generated text message to other aircraft in a geographic area relevant to the current flight plan and/or the alternate flight plan, to inform relevant parties of the changes to the current flight plan.

Figure 2:
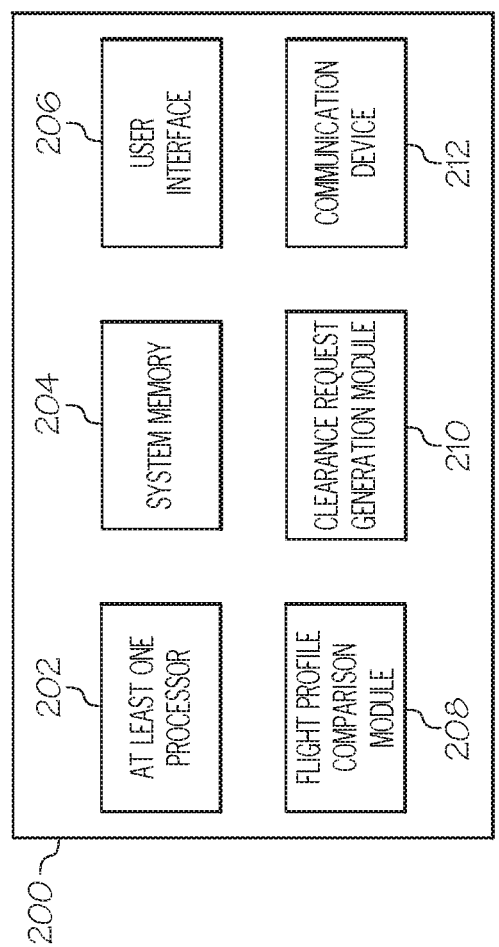
FIG. 2 is a computing device for use in a system for automatically generating clearance requests, in accordance with the disclosed embodiments.

FIG. 2 is a computing device 200 for use in a system for automatically generating clearance requests, in accordance with the disclosed embodiments. The computing device 200 is generally used onboard an aircraft to obtain changes to a current flight plan and to generate and transmit a text message that includes a clearance request for the changes to the current flight plan. It should be noted that the computing device 200 can be implemented with the computing device 104 depicted in FIG. 1. In this regard, the computing device 200 shows certain elements and components of the computing device 104 in more detail.

The computing device 200 generally includes, without limitation: at least one processor 202; system memory 204; a user interface 206; a flight profile comparison module 208; a clearance request generation module 210; and a communication device 212. These elements and features of the computing device 200 may be operatively associated with one another, coupled to one another, or otherwise configured to cooperate with one another as needed to support the desired functionality—in particular, generating and transmitting a text-based clearance request, as described herein. For ease of illustration and clarity, the various physical, electrical, and logical couplings and interconnections for these elements and features are not depicted in FIG. 2. Moreover, it should be appreciated that embodiments of the computing device 200 will include other elements, modules, and features that cooperate to support the desired functionality. For simplicity, FIG. 2 only depicts certain elements that relate to the fuel tankering recommendation-generating techniques described in more detail below.

The at least one processor 202 may be implemented or performed with one or more general purpose processors, a content addressable memory, a digital signal processor, an application specific integrated circuit, a field programmable gate array, any suitable programmable logic device, discrete gate or transistor logic, discrete hardware components, or any combination designed to perform the functions described here. In particular, the at least one processor 202 may be realized as one or more microprocessors, controllers, microcontrollers, or state machines. Moreover, the at least one processor 202 may be implemented as a combination of computing devices, e.g., a combination of digital signal processors and microprocessors, a plurality of microprocessors, one or more microprocessors in conjunction with a digital signal processor core, or any other such configuration.

The at least one processor 202 is communicatively coupled to the system memory 204. The system memory 204 is configured to store any obtained or generated data associated with a current flight plan, changes to the current flight plan, alternate flight plans, a standardized format for text-based messages, and other data associated with the system for generating and transmitting text-based clearance requests. The system memory 204 may be realized using any number of devices, components, or modules, as appropriate to the embodiment. Moreover, the computing device 200 could include system memory 204 integrated therein and/or a system memory 204 operatively coupled thereto, as appropriate to the particular embodiment. In practice, the system memory 204 could be realized as RAM memory, flash memory, EPROM memory, EEPROM memory, registers, a hard disk, a removable disk, or any other form of storage medium known in the art. In certain embodiments, the system memory 204 includes a hard disk, which may also be used to support functions of the computing device 200. The system memory 204 can be coupled to the at least one processor 202 such that the at least one processor 202 can read information from, and write information to, the system memory 204. In the alternative, the system memory 204 may be integral to the at least one processor 202. As an example, the at least one processor 202 and the system memory 204 may reside in a suitably designed application-specific integrated circuit (ASIC).

The user interface 206 may include or cooperate with various features to allow a user to interact with the computing device 200. Accordingly, the user interface 206 may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the computing device 200. For example, the user interface 206 could be manipulated by an operator to provide user-requested changes to a current flight plan and/or a user selection of an alternate flight plan, which are then used to generate a text-based clearance request message, as described herein.

In certain embodiments, the user interface 206 may include or cooperate with various features to allow a user to interact with the computing device 200 via graphical elements rendered on a display element. Accordingly, the user interface 206 may initiate the creation, maintenance, and presentation of a graphical user interface (GUI). In certain embodiments, the display element implements touch-sensitive technology for purposes of interacting with the GUI. Thus, a user can manipulate the GUI by moving a cursor symbol rendered on the display element, or by physically interacting with the display element itself for recognition and interpretation, via the user interface 206.

The flight profile comparison module 208 is configured to identify an optimal flight profile or an alternate flight profile, which may differ from a current flight profile of the aircraft. The flight profile comparison module 208 functions to (i) receive meteorological data, via the communication device 212, and to create an "optimal" flight profile, based on the received meteorological data; and (ii) receive user input data associated with a user-requested, alternate flight profile. The flight profile comparison module 208 is further configured to compare the current flight plan or profile to the created profile based on changes to the current flight plan, and to identify whether the alternate or optimal flight plan includes characteristics more beneficial than the characteristics associated with the current flight plan. In the case of an alternate flight plan or an optimal flight plan including such beneficial characteristics, the computing device 200 determines that the alternate flight profile or the optimal flight profile is preferable to the current flight plan, and takes additional action using the clearance request generation module 210.

The clearance request generation module 210 is configured to create a text message that includes a clearance request, based on obtained changes to a current flight plan of the aircraft. Details included in the text-based clearance request message may include at least aircraft identification data and data associated with the requested change, including revised time estimates associated with waypoints of the current flight plan. The clearance request generation module 210 generally uses a standardized format for the text-based clearance requests, which may include particular data fields, a particular order of the data fields, acronyms or other relevant and meaningful terminology used to provide information in the data fields, or the like. The standardized format is used such that the transmitted text messages are readily recognized and easily interpreted and understood by recipient, including air traffic control (ATC) and/or other aircraft in the geographic area associated with the flight plan. In certain embodiments, the clearance request generation module 210 generates the clearance request when the flight profile comparison module 208 has determined that the optimal flight profile has beneficial characteristics, as described previously with regard to the flight profile comparison module 208. In some embodiments, the clearance request generation module 210 generates the clearance request when a user request is received, via the user interface 206.

In practice, the flight profile comparison module 208 and/or the clearance request generation module 210 may be implemented with (or cooperate with) the at least one processor 202 to perform at least some of the functions and operations described in more detail herein. In this regard, the flight profile comparison module 208 and/or the clearance request generation module 210 may be realized as suitably written processing logic, application program code, or the like.

The communication device 212 is suitably configured to communicate data between the computing device 200 and one or more remote servers and one or more avionics systems onboard an aircraft. The communication device 212 may transmit and receive communications over a wireless local area network (WLAN), the Internet, a satellite uplink/downlink, a cellular network, a broadband network, a wide area network, or the like. As described in more detail below, data received by the communication device 212 may include, without limitation: aircraft identification data; current flight plan data; optimized flight plan data; alternate flight plan data; meteorological data associated with a current flight plan, an optimized flight plan, and/or an alternate flight plan; and other data compatible with the computing device 200. Data provided by the communication device 212 may include, without limitation, flight plan comparison data, text-based clearance request messages, and the like.

Figure 3:
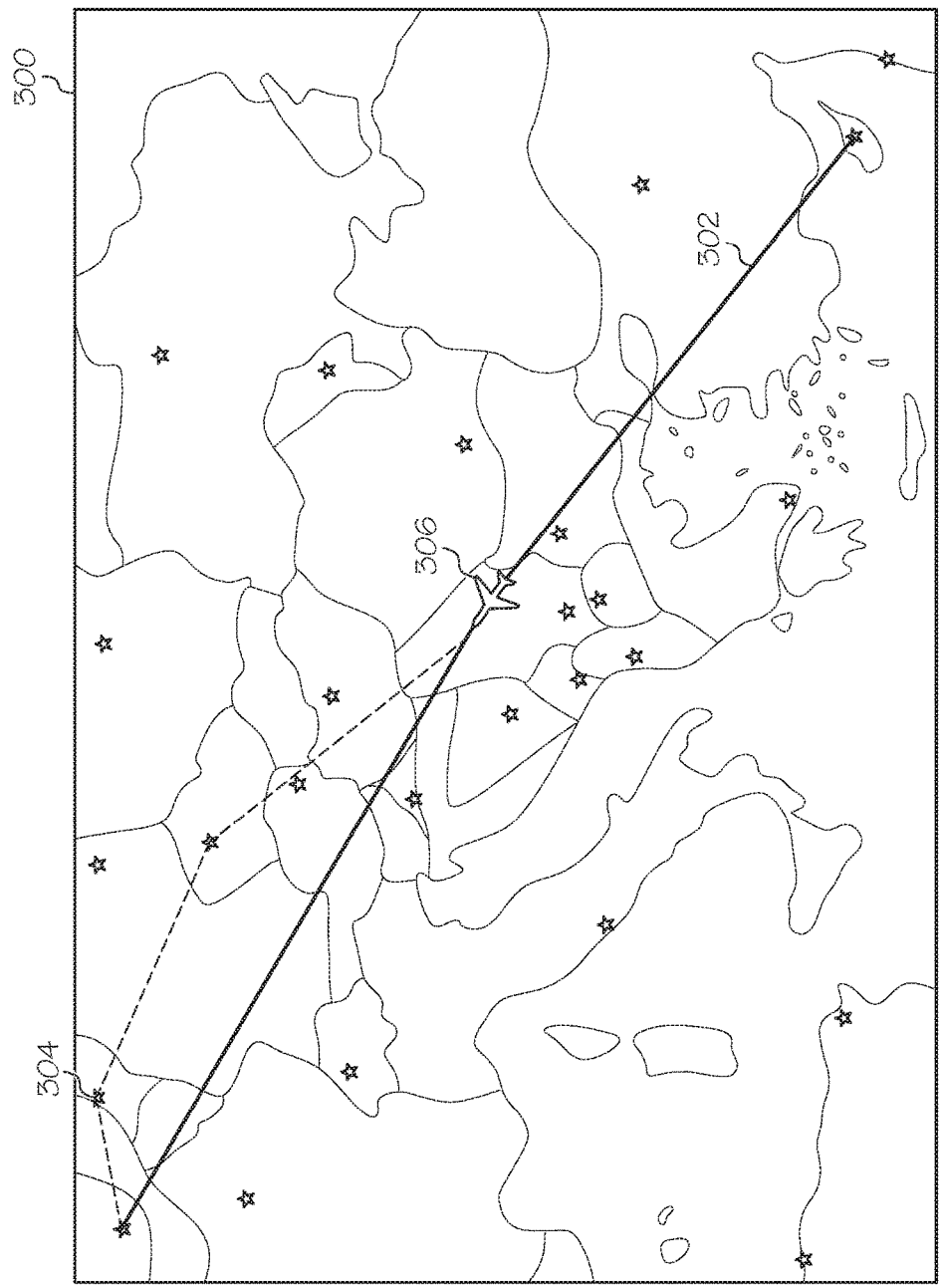
FIG. 3 is a diagram of a primary trajectory and an updated trajectory for which a clearance request is automatically generated, in accordance with the disclosed embodiments.

FIG. 3 is a diagram of a map display 300 that depicts an exemplary embodiment of a primary trajectory 302 and an updated trajectory 304 for which a clearance request is automatically generated. In the example shown, an aircraft 306 is in-flight and traveling using the primary trajectory 302, and is currently located in Serbian airspace just before reaching Belgrade. At the current location of the primary trajectory 302, the aircraft 306 receives updated meteorological data, and a computing device (see FIG. 1, reference 104; FIG. 2, reference 200) onboard the aircraft 306 computes a new optimum profile based on the received, updated meteorological data. As described previously, the computing device may be implemented using a computing system integrated into the aircraft 306 or a standalone computing device (e.g., a tablet computer or laptop computer) communicatively coupled to the aircraft onboard avionics and configured to store, maintain, and execute an electronic flight bag (EFB) application to perform flight plan analysis and text-based clearance request message generation, as described herein.

In the example shown, when an optimal flight profile is different from a current flight profile or a current primary trajectory 302 (i.e., when the optimal flight profile includes vertical profile changes and/or lateral profile changes to the current flight profile), the EFB application creates a message about the one or more changes to the flight plan which is then presented for viewing by the flight crew. The flight crew views the presented message and provides user input to the EFB application to accept the presented changes to the current flight profile. The user input selection initiates a transmission of the message, which includes a clearance request for the new flight plan (e.g., the flight plan changes, the updated trajectory 304) to the appropriate air traffic control (ATC) center.

The ATC receives the text-based clearance request message, interprets the requested flight plan changes from the received text-based clearance request message, and distributes information associated with the change of the flight plan (via ground systems) to other ATC along the updated trajectory 304, and coordinates change of the flight plan. After coordination the ATC makes decision and potentially issues new clearance. After receiving the new clearance from ATC, the flight crew may start to change the flight profile in accordance with the new clearance, from the position at which a requested change of route has to commence.

Figure 4:
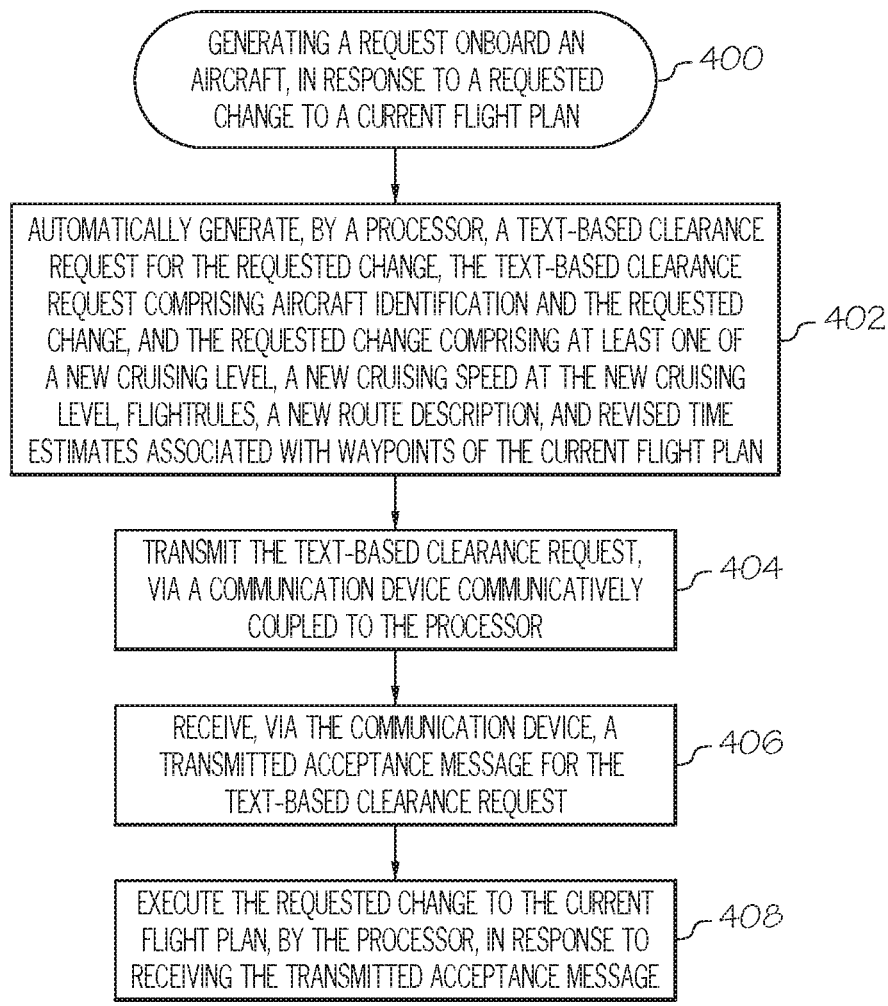
FIG. 4 is a flow chart that illustrates an embodiment of a process for generating a request onboard an aircraft, in response to a requested change to a current flight plan.

FIG. 4 is a flow chart that illustrates an embodiment of a process 400 for generating a request onboard an aircraft, in response to a requested change to a current flight plan. First, the process 400 automatically generates, by a processor, a text-based clearance request for the requested change, the text-based clearance request comprising aircraft identification and the requested change comprising at least one of a new cruising level, a new cruising speed at the new cruising level, flight rules, a new route description, and revised time estimates associated with waypoints of the current flight plan (step 402). Here, the process 400 obtains information indicating that a change to a current flight plan has been requested. In some embodiments of the process 400, the change to the current flight plan may be requested by a system onboard the aircraft (e.g., a flight management system (FMS), an obstacle collision avoidance system (OCAS)) and/or a computing device onboard the aircraft, as described in more detail with respect to FIG. 5. In some embodiments, the change to the current flight plan is one or more user input changes received via a user interface communicatively coupled to the processor, wherein the requested change comprises the one or more user input changes.

Once the process 400 obtains information indicating that a change to the current flight plan has been requested, the process 400 creates a text-based clearance request message that includes detail associated with the change. The process 400 generates the text-based clearance message using a standardized format for ease of interpretation by recipients (e.g., air traffic control (ATC), other aircraft traveling in a geographic area associated with the current flight plan, the optimal flight plan, or the optimal flight plan), wherein the standardized format may include predefined data fields and predefined terminology and acronyms for use in completing the data fields.

Next, the process 400 transmits the text-based clearance request, via a communication device communicatively coupled to the processor (step 404). The process 400 may transmit the text-based clearance request to ATC and other aircraft traveling in a geographic area associated with the current flight plan, the optimal flight plan, or the optimal flight plan. The process 400 generally transmits the text-based clearance message using an aircraft onboard computing device, as described previously with regard to FIGS. 1-2. In certain embodiments, the process 400 receives, via the communication device, a transmitted acceptance message for the text-based clearance request (step 406), from ATC, and then the process 400 executes the requested change to the current flight plan, by the processor, in response to receiving the transmitted acceptance message (step 408).

Figure 5:
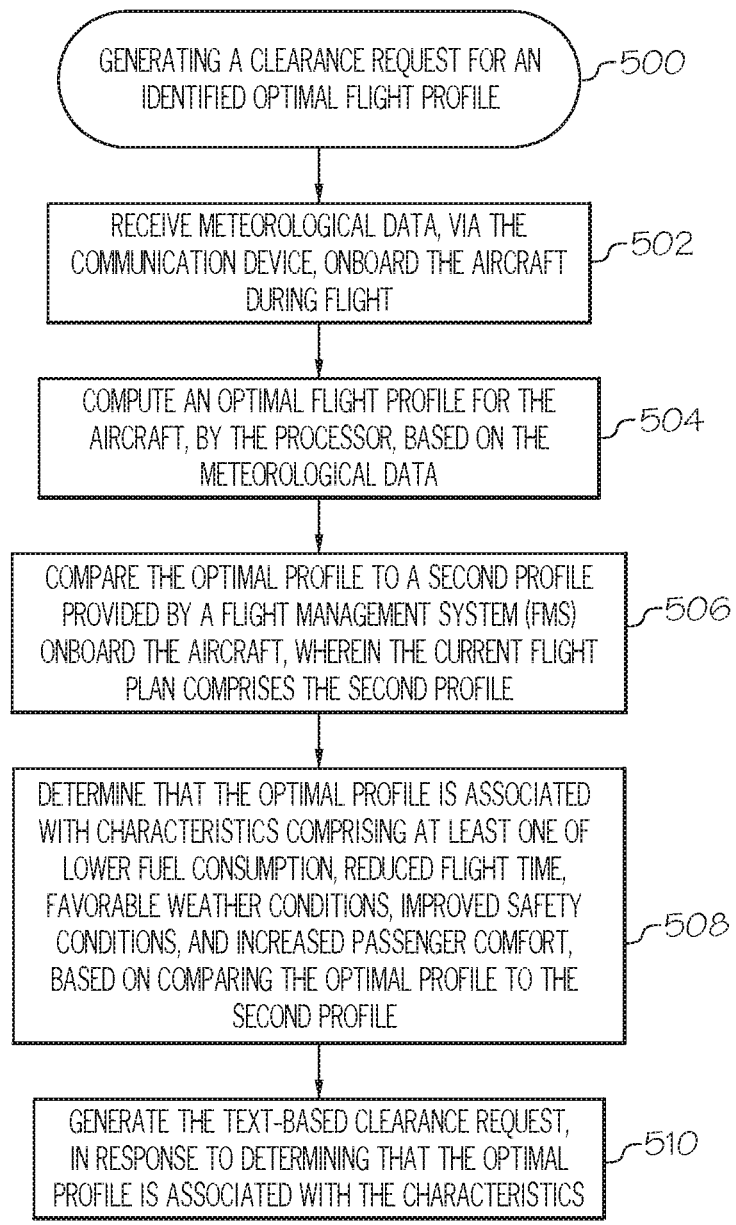
FIG. 5 is a flow chart that illustrates an embodiment of a process for generating a clearance request for an identified optimal flight profile.

FIG. 5 is a flow chart that illustrates an embodiment of a process 500 for generating a clearance request for an identified optimal flight profile. The process 500 receives meteorological data, via the communication device, onboard the aircraft during flight (step 502). The process 500 computes an optimal flight profile for the aircraft, by the processor, based on the meteorological data (step 504). The optimal flight profile may be a vertical flight profile, a lateral flight profile, or may include elements of both a vertical flight profile and a lateral flight profile. The optimal flight profile is generally computed in order to identify a flight profile providing lower fuel consumption, reduced flight time, favorable weather conditions, improved safety conditions, increased passenger comfort, and the like.

The process 500 then compares the optimal flight profile to a second profile provide by a flight management system (FMS) onboard the aircraft, wherein the current flight plan comprises the second profile (step 506). Here, the process 500 compares the newly-computed optimal profile to the current flight plan to determine whether the optimal profile provides the beneficial characteristics sought when originally computed (e.g., lower fuel consumption, reduced flight time, favorable weather conditions, improved safety conditions, and increased passenger comfort).

After comparing the optimal flight profile to the second profile (step 506), the process 500 then determines that the optimal profile is associated with characteristics comprising at least one of lower fuel consumption, reduced flight time, favorable weather conditions, improved safety conditions, and increased passenger comfort, based on comparing the optimal profile to the second profile (step 508).

In certain embodiments, after the process 500 performs the comparison, the process 500 requests user input approval before proceeding to generate a text-based clearance request (step 510). In this case, the process 500 receives a user input selection of the optimal profile, via a user interface communicatively coupled to the processor, and generates the text-based clearance request, by the processor, in response to the user input selection.

The various tasks performed in connection with processes 400-500 may be performed by software, hardware, firmware, or any combination thereof. For illustrative purposes, the preceding descriptions of processes 400-500 may refer to elements mentioned above in connection with FIGS. 1-3. In practice, portions of processes 400-500 may be performed by different elements of the described system. It should be appreciated that processes 400-500 may include any number of additional or alternative tasks, the tasks shown in FIGS. 4-5 need not be performed in the illustrated order, and processes 400-500 may be incorporated into a more comprehensive procedure or process having additional functionality not described in detail herein. Moreover, one or more of the tasks shown in FIGS. 4-5 could be omitted from an embodiment of the processes 400-500 as long as the intended overall functionality remains intact.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. The program or code segments can be stored in a processor-readable medium or transmitted by a computer data signal embodied in a carrier wave over a transmission medium or communication path. The "computer-readable medium", "processor-readable medium", or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

The following description refers to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. Likewise, unless expressly stated otherwise, "connected" means that one element/node/feature is directly joined to (or directly communicates with) another element/node/feature, and not necessarily mechanically. Thus, although the schematic shown in FIG. 2 depicts one exemplary arrangement of elements, additional intervening elements, devices, features, or components may be present in an embodiment of the depicted subject matter.

For the sake of brevity, conventional techniques related to signal processing, data transmission, signaling, network control, and other functional aspects of the systems (and the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

Some of the functional units described in this specification have been referred to as "modules" in order to more particularly emphasize their implementation independence. For example, functionality referred to herein as a module may be implemented wholly, or partially, as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like. Modules may also be implemented in software for execution by various types of processors. An identified module of executable code may, for instance, comprise one or more physical or logical modules of computer instructions that may, for instance, be organized as an object, procedure, or function. Nevertheless, the executables of an identified module need not be physically located together, but may comprise disparate instructions stored in different locations that, when joined logically together, comprise the module and achieve the stated purpose for the module. Indeed, a module of executable code may be a single instruction, or many instructions, and may even be distributed over several different code segments, among different programs, and across several memory devices. Similarly, operational data may be embodied in any suitable form and organized within any suitable type of data structure. The operational data may be collected as a single data set, or may be distributed over different locations including over different storage devices, and may exist, at least partially, merely as electronic signals on a system or network.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method for generating a request onboard an aircraft, by a computing device comprising at least a processor communicatively coupled to system memory and a communication device, the method comprising:
   executing an Electronic Flight Bag (EFB) application, by the processor of the computing device;
   in response to a requested change to a current flight plan by the EFB application,
      automatically generating, by the processor via the EFB application, a text-based clearance request for the requested change, the text-based clearance request comprising aircraft identification and the requested change, and the requested change comprising at least one of a new cruising level, a new cruising speed at the new cruising level, flight rules, a new route description, and revised time estimates associated with waypoints of the current flight plan; and
      transmitting the text-based clearance request to air traffic control (ATC) and other aircraft in an applicable geographic area associated with the current flight plan and the requested change, using a wireless communication network, by the communication device of the computing device, via the EFB application.

2. The method of claim 1, wherein the requested change comprises at least one of a vertical change and a lateral change to the current flight plan.

3. The method of claim 1, further comprising:
   receiving, via the communication device, meteorological data onboard the aircraft during the flight; and
   computing an optimal flight profile for the aircraft, by the processor, based on the meteorological data;
   wherein the text-based clearance request comprises a request to replace the current flight plan with the optimal flight profile, and wherein the change comprises differences between the current flight plan and the optimal profile.

4. The method of claim 3, further comprising:
   comparing the optimal profile to a second profile provided by a flight management system (FMS) onboard the aircraft, wherein the current flight plan comprises the second profile; and
   determining that the optimal profile is associated with characteristics comprising at least one of lower fuel consumption, reduced flight time, favorable weather conditions, improved safety conditions, and increased passenger comfort, based on the comparing; and
   generating the text-based clearance request, in response to determining that the optimal profile is associated with the characteristics.

5. The method of claim 3, further comprising:
   receiving user input selection of the optimal profile, via a user interface communicatively coupled to the processor; and
   generating the text-based clearance request, by the processor, in response to the user input selection.

6. The method of claim 1, further comprising:
   receiving, via a user interface communicatively coupled to the processor, one or more user input changes to the current flight plan;
   wherein the requested change comprises the one or more user input changes.

7. The method of claim 1, further comprising:
   receiving, via the communication device, a transmitted acceptance message for the text-based clearance request; and
   executing the requested change to the current flight plan, by the processor, in response to receiving the transmitted acceptance message.

8. A system for generating a request onboard an aircraft, the system comprising a computing device that includes:
   system memory, configured to store an Electronic Flight Bag (EFB) application for generating text-based clearance requests for potential changes to a current flight plan;
   a communication device, configured to transmit data from the aircraft to air traffic control (ATC);
   at least one processor, communicatively coupled to the system memory and the communication device, the at least one processor configured to:
      execute an Electronic Flight Bag (EFB) application;
      in response to a requested change to a current flight plan received by the EFB application,
         automatically generate, via the EFB application, a text-based clearance request for the requested change, the text-based clearance request comprising aircraft identification and the requested change, and the requested change comprising at least one of a new cruising level, a new cruising speed at the new cruising level, flight rules, a new route description, and revised time estimates associated with waypoints of the current flight plan; and
         transmit the text-based clearance request to air traffic control (ATC) and other aircraft in an applicable geographic area associated with the current flight plan and the requested change, via the communication device of the computing device using the EFB application.

9. The system of claim 8, wherein the requested change comprises at least one of a vertical change and a lateral change to the current flight plan.

10. The system of claim 8, wherein the at least one processor is further configured to:
    receive, via the communication device, meteorological data onboard the aircraft during the flight; and
    compute an optimal flight profile for the aircraft, based on the meteorological data;
    wherein the text-based clearance request comprises a request to replace the current flight plan with the optimal flight profile, and wherein the change comprises differences between the current flight plan and the optimal profile.

11. The system of claim 10, wherein the at least one processor is further configured to:
  compare the optimal profile to a second profile provided by a flight management system (FMS) onboard the aircraft, wherein the current flight plan comprises the second profile; and
  determine that the optimal profile is associated with characteristics comprising at least one of lower fuel consumption, reduced flight time, favorable weather conditions, improved safety conditions, and increased passenger comfort, based on the comparing; and
  generate the text-based clearance request, in response to determining that the optimal profile is associated with the characteristics.

12. The system of claim 10, wherein the system further comprises a user interface communicatively coupled to the at least one processor; and
  wherein the at least one processor is further configured to:
    receive user input selection of the optimal profile, via the user interface; and
    generate the text-based clearance request, in response to the user input selection.

13. The system of claim 8, wherein the system further comprises a user interface communicatively coupled to the at least one processor; and
  wherein the at least one processor is further configured to receive, via the user interface, one or more user input changes to the current flight plan, wherein the requested change comprises the one or more user input changes.

14. The system of claim 8, wherein the at least one processor is further configured to:
  receive, via the communication device, a transmitted acceptance message for the text-based clearance request; and
  execute the requested change to the current flight plan, in response to receiving the transmitted acceptance message.

15. A non-transitory, computer-readable medium containing instructions thereon, which, when executed by a processor of a computing device, perform a method comprising:
  executing an Electronic Flight Bag (EFB) application, by the processor of the computing device;
  receiving a request for one or more changes to a current flight plan, by the processor onboard an aircraft, via the EFB application;
  generating, by the processor via the EFB application, a text message comprising a clearance request for the one or more changes to the current flight plan; and
  transmitting the text message to air traffic control (ATC) and other aircraft in an applicable geographic area associated with the current flight plan and the requested change, via a communication device communicatively coupled to the processor, using the EFB application.

16. The non-transitory, computer-readable medium of claim 15, wherein the method further comprises:
  receiving, via the communication device, meteorological data onboard the aircraft during the flight; and
  computing an optimal flight profile for the aircraft, by the processor, based on the meteorological data;
  wherein the text message comprises a request to replace the current flight plan with the optimal flight profile, and wherein the one or more changes comprises differences between the current flight plan and the optimal profile.

17. The non-transitory, computer-readable medium of claim 16, wherein the method further comprises:
  comparing the optimal profile to a second profile provided by a flight management system (FMS) onboard the aircraft, wherein the current flight plan comprises the second profile; and
  determining that the optimal profile is associated with characteristics comprising at least one of lower fuel consumption, reduced flight time, favorable weather conditions, improved safety conditions, and increased passenger comfort, based on the comparing; and
  generating the text message, in response to determining that the optimal profile is associated with the characteristics.

18. The non-transitory, computer-readable medium of claim 16, wherein the method further comprises:
  receiving user input selection of the optimal profile, via a user interface communicatively coupled to the processor; and
  generating the text message, by the processor, in response to the user input selection.

19. The non-transitory, computer-readable medium of claim 15, wherein the method further comprises:
  receiving, via a user interface communicatively coupled to the processor, one or more user input changes to the current flight plan;
  wherein the requested change comprises the one or more user input changes.

20. The non-transitory, computer-readable medium of claim 15, wherein the method further comprises:
  receiving, via the communication device, a transmitted acceptance message for the text message; and
  executing the requested change to the current flight plan, by the processor, in response to receiving the transmitted acceptance message.

* * * * *